United States Patent [19]

Maravetz

[11] 4,051,254
[45] Sept. 27, 1977

[54] SULFONAMIDO-AND AMIDOPHENYL N-METHYLCARBAMATES AND USE AS INSECTICIDES

[75] Inventor: Lester L. Maravetz, Westfield, N.J.
[73] Assignee: Mobil Oil Corporation, New York, N.Y.
[21] Appl. No.: 642,265
[22] Filed: Dec. 19, 1975
[51] Int. Cl.$^2$ .................. C07D 307/68; A01N 9/20; C07C 125/06; C07C 143/75
[52] U.S. Cl. .................. 424/285; 424/300; 260/347.4; 560/136
[58] Field of Search ............ 260/347.4, 479 C, 471 C; 424/285, 300

[56] References Cited

U.S. PATENT DOCUMENTS

| 3,037,993 | 6/1962 | Shulgin | 260/479 C |
|---|---|---|---|
| 3,450,745 | 6/1969 | Payne et al. | 260/471 |
| 3,639,474 | 2/1972 | Harrington et al. | 260/479 C |
| 3,792,994 | 2/1974 | Baker et al. | 260/471 C |
| 3,836,564 | 9/1974 | Baker et al. | 260/479 C |
| 3,872,157 | 3/1975 | Brokke et al. | 260/347.4 |

FOREIGN PATENT DOCUMENTS

| 2,163,459 | 7/1973 | Germany | 260/479 C |

*Primary Examiner*—Henry R. Jiles
*Assistant Examiner*—Bernard Dentz
*Attorney, Agent, or Firm*—Charles A. Huggett; Hastings S. Trigg

[57] ABSTRACT

There are provided phenyl N-methylcarbamates substituted in the 4-position with groups, such as alkanesulfamido, haloalkanesulfamido, alkoxyalkanamido, haloalkanamido, alkylthioalkanamido, or furoylamido. These compounds are effective for the control of several insect species as systemic and stomach poison insecticides, as larvicides, and as ovicides.

39 Claims, No Drawings

SULFONAMIDO-AND AMIDOPHENYL N-METHYLCARBAMATES AND USE AS INSECTICIDES

BACKGROUND OF THE INVENTION

1. Field of the Invention

This invention is directed to certain substituted phenyl N-methylcarbamates and their use as insecticides, larvicides, and ovicides.

2. Description of the Prior Art

In German Pat. No. 1,147,572, there are described aminosulfonylphenyl and dimethylaminosulfonylphenyl N,N-dimethyl carbamates. The para-aminosulfonylphenyl N,N-diethyl carbamate is disclosed to give a 50% kill of aphids when applied at a relatively high dosage of 100 ppm. These patentees showed 100% kill systemically, but at a dosage of 1,000 ppm., i.e., 20 times the maximum dosage (50 ppm.) used by applicant to obtain 100% kill systemically.

U.S. Pat. No. 3,037,993 discloses certain amidophenyl N-methylcarbamates as having insecticidal activity. Such activity is shown only for the formamidophenyl carbamates. There is no teaching that the acyl moiety can be substituted as in the present invention, i.e., with alkoxy, halo, phenoxy, alkylthio, or furyl.

In U.S. Pat. No. 3,836,570 there are disclosed m-alkanamidophenyl carbamates, useful as herbicides. The patentee presents $LD_{50}$ data to show that the analogous parasubstituted derivatives are decidedly inferior against the housefly.

Insofar as is now known, it has not been proposed or suggested that the compounds of this invention would have the high degree of insecticidal activity that is demonstrated hereinafter.

SUMMARY OF THE INVENTION

This invention provides compounds having the structure:

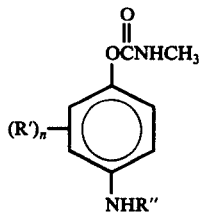

wherein R' is H, ($C_1$–$C_5$) alkyl, Cl, or ($C_1$–$C_4$) alkoxy; $n$ is 1 to 3; R" is —$SO_2$R''', wherein R''' is ($C_1$–$C_4$) alkyl, ($C_3$–$C_6$) cycloalkyl, ($C_1$–$C_4$) haloalkyl, phenyl, or tolyl or R" is

wherein R'''' is ($C_1$–$C_4$) alkoxy ($C_1$–$C_4$) alkyl, ($C_1$–$C_4$) haloalkyl, phenoxy ($C_1$–$C_4$) alkyl, ($C_1$–$C_4$) alkylthio ($C_1$–$C_4$) alkyl, furyl, ($C_1$–$C_4$) alkoxy, ($C_3$–$C_6$) cycloalkyl.

DESCRIPTION OF SPECIFIC EMBODIMENTS

In addition to the compounds described in the working examples, non-limiting examples of the compounds of this invention includes:

3-Ethyl-4-(ethanesulfonamido)phenyl N-methylcarbamate
3-Isopropyl-4-(butanesulfonamido)phenyl N-methylcarbamate
3-t-Butyl-4-(benzenesulfonamido)phenyl N-methylcarbamate
3,5-Dipropyl-4-(propanesulfonamido)phenyl N-methylcarbamate
2,5-Diethyl-4-(ethanesulfonamido)phenyl N-methylcarbamate
2,3,5-Trimethyl-4-(ethanesulfonamido)phenyl N-methylcarbamate
2-Chloro-4-(ethanesulfonamido)phenyl N-methylcarbamate
2,5-Dichloro-4-(ethanesulfonamido)phenyl N-methylcarbamate
3-t-Butyl-4-(ethanesulfonamido)phenyl N-methylcarbamate
3-Methyl-4-(cyclopropanesulfonamido)phenyl N-methylcarbamate
3-Methyl-4-(cyclohexanesulfonamido)phenyl N-methylcarbamate
2-Methoxy-4-(propanesulfonamido)phenyl N-methylcarbamate
3-Methoxy-4-(ethanesulfonamido)phenyl N-methylcarbamate
3-Isobutoxy-4-(propanesulfonamido)phenyl N-methylcarbamate
3,5-Dimethoxy-4-(benzenesulfonamido)phenyl N-methylcarbamate
2,5-Dimethyl-4-(methanesulfonamido)phenyl N-methylcarbamate
3,5-Dipropoxy-4-(ethanesulfonamido)phenyl N-methylcarbamate
3-Ethyl-4-(methoxyacetamido)phenyl N-methylcarbamate
3-Isopropyl-4-(ethoxyacetamido)phenyl N-methylcarbamate
3-t-Butyl-4-(n-propoxyacetamido)phenyl N-methylcarbamate
3,5-Dipropyl-4-(α-phenoxypropionamido)phenyl N-methylcarbamate
2,5-Diethyl-4-(trichloroacetamido)phenyl N-methylcarbamate
2,3,5-Trimethyl-4-(dichloroacetamido)phenyl N-methylcarbamate
2-Chloro-4-(3-chloropropionamido)phenyl N-methylcarbamate
2,5-Dichloro-4-(trifluoroacetamido)phenyl N-methylcarbamate
3,5-Dimethyl-4-(trifluoroacetamido)phenyl N-methylcarbamate
3-Methoxy-4-(chloroacetamido)phenyl N-methylcarbamate
3-Isobutoxy-4-(methylthioacetamido)phenyl N-methylcarbamate
3,5-Dimethoxy-4-(chlorodifluoroacetamido)phenyl N-methylcarbamate
3,5-Dimethyl-4-(α-chloropropionamido)phenyl N-methylcarbamate
3,5-Dimethyl-4-(2-furoylamido)phenyl N-methylcarbamate
2,5-Dimethyl-4-(carbethoxyamino)phenyl N-methylcarbamate
3-(1-Methylbutyl)-4-(ethanesulfonamido)phenyl N-methylcarbamate
2-Isopropoxy-4-(ethanesulfonamido)phenyl N-methylcarbamate 3-sec-Butyl-4-(ethanesulfonamido)phenyl N-methylcarbamate 2-sec-Butyl-4-(propanesulfonamido)phenyl N-methylcarbamate 2-Methyl-5-isopropyl-4-(methanesulfonamido)phenyl N-methylcarbamate 2-isopropoxy-4-(methoxyacetamido)phenyl N-methylcarbamate 2-isopropoxy-4-(chlorodifluoroacetamido)phenyl N-methylcarbamate 3-t-Butyl-4-(methoxyacetamido)phenyl N-methylcarbamate 3-t-Butyl-4-(carbethoxyamino)phenyl N-methylcarbamate 3-(1-Methylbutyl)-4-(methoxyacetamido)phenyl N-methylcarbamate 3-(1-Methylbutyl)-4-(chloroacetamido)phenyl N-methylcarbamate 2-sec-Butyl-4-(methoxyacetamido)phenyl N-methylcarbamate 3,5-Dimethyl-4-(carbomethoxyamino)phenyl N-methylcarbamate 3-t-Butyl-4-(chlorodifluoracetamido)phenyl N-methylcarbamate 3-Methyl-4-(cyclohexanecarboxamido)phenyl N-methylcarbamate.

Table 1 summarizes the reaction sequences by which the compounds of this invention may be synthesized.

Sequence A involves the carbamylation of substituted nitrophenols (I) with methyl isocyanate using solvents such as benzene, toluene, acetone, chloroform, acetonitrile, and tetrahydrofuran. Catalysts which may be helpful in this reaction are amines such as triethylamine and pyridine, and dibutyltindiacetate. As an alternative to the use of methyl isocyanate, I may be sequentially reacted with phosgene and methylamine to form product II.

In the second step of Sequence A, the nitro group of II is reduced catalytically to the corresponding amino derivative III using hydrogen under pressure along with suitable supported or unsupported platinum metal catalysts, such as palladium, platinum, rhodium, and ruthenium. Solvents which may be used to advantage in this reaction are methanol, ethanol, ethyl acetate, and dioxane.

The intermediate III is reacted either with appropriate acid chlorides or acid anhydrides, or sulfonyl chlorides to yield the final substituted phenyl N-methylcarbamates IV and V, which are subject insecticides of this application. In certain cases tertiary amines, such as triethylamine or pyridine, may be used as HCl acceptors. Suitable solvents in these reactions are benzene, toluene, acetone, chloroform, methylene chloride, acetonitrile, tetrahydrofuran, and pyridine.

As an alternative route to compounds IV, Sequence B may be utilized. In this case substituted aminophenols VI (Certain ones of which may be prepared according to method of A. T. Shulgin, U.S. Pat. No. 3,084,098) are selectively acylated at nitrogen with R''''COCl to yield phenols VII. These in turn upon carbamylation with methyl isocyanate (or stepwise use of phosgene and methylamine) give the insecticidal carbamates IV. Solvents listed in the description of Sequence A are also suitable in B.

TABLE I
Synthesis of Substituted Phenyl N-Methylcarbamates

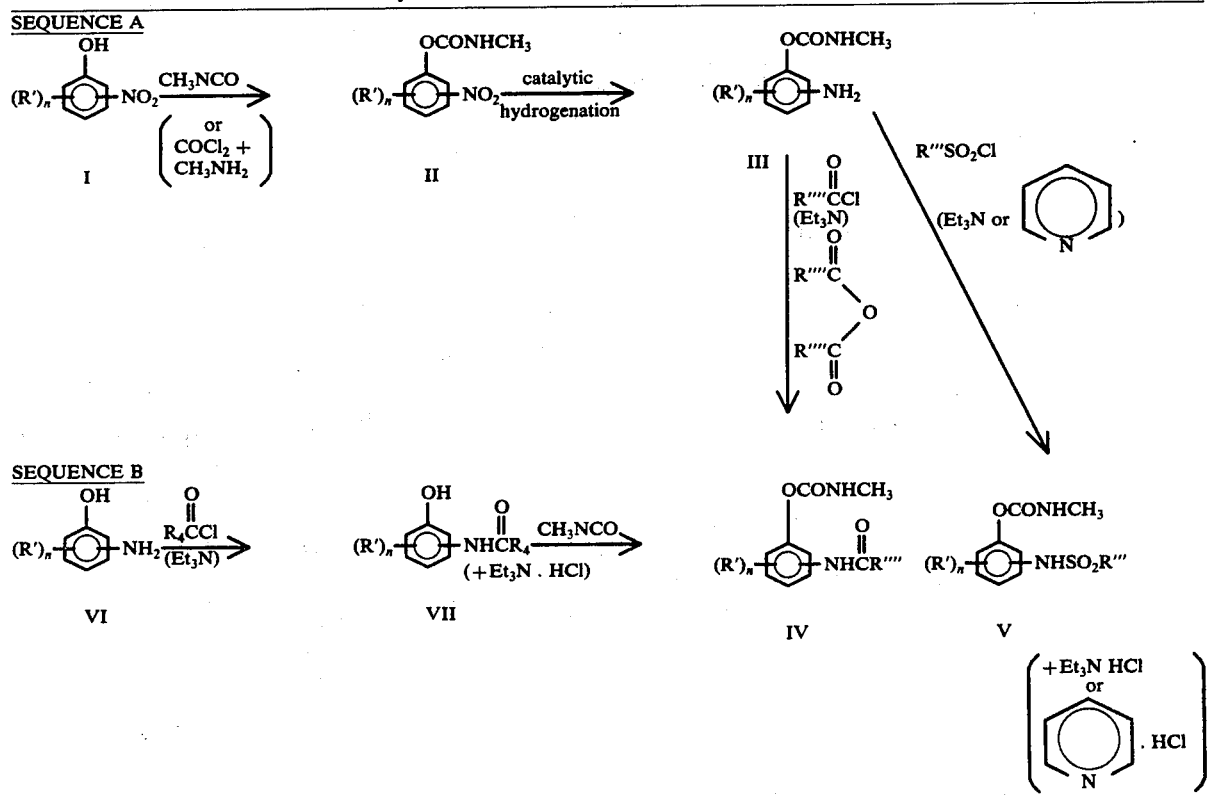

The following working examples demonstrate the aforedescribed synthesis of the compounds of this invention and the manipulations and techniques involved. Data are also presented demonstrating the effectiveness of typical compounds of this invention against harmful insects and their ova and larvae.

EXAMPLE 1

Synthesis of 3-methyl-4-(methanesulfonamido)phenyl N-methylcarbamate

A. 3-methyl-4-nitrophenyl N-methylcarbamate

3-Methyl-4-nitrophenol (46.0g., 0.30 mole) was dissolved in tetrahydrofuran (200 ml.) and triethylamine (2 ml.). To this solution was added dropwise methylisocyanate (18.8g., 0.33 mole, 25 ml.) which resulted in an exotherm to about 40° C. Refluxing for one hour, followed by quenching in excess water, yieldig a light tan precipitate. After filtration and drying the material (51g.) melted at .99°–101° C.

B. 3-methyl-4-aminophenyl N-methylcarbamate

A Parr hydrogenation bottle was charged with 3-methyl-4-nitrophenyl N-methylcarbamate (21g., 0.1 mole), ethyl acetate (150 ml.), and 5% palladium on charcoal catalyst (1.0g.). The slurry was hydrogenated in a low pressure Parr hydrogenation apparatus with an intial pressure of 60 psi.

Theoretical hydrogen uptake was achieved in about 70 minutes. The product after isolation and recrystallization from benzene was a tan granular solid (m.p. 121°–24° C.) which was soluble in 5% HCl. Infared analysis (KBr) indicated the retention of the carbonyl group (5.8 $\mu$).

C. 3-methyl-4-(methanesulfonamido)phenyl N-methylcarbamate

A flask was charged with 3-methyl-4-aminophenyl N-methylcarbamate (3.0g., 0.0166 mole), triethylamine (1.83g., 0.018 mole, 2.53 ml.) and about 100 ml. of benzene. To this slurry was added methanesulfonyl chloride and after one hour at reflux the mixture was cooled and filtered. The solids were stirred vigorously with water to dissolve any residual by-product triethylamine hydrochloride. Refiltration and drying gave 2.3g. of the desired product (m.p. 167°–69° C.).

EXAMPLE 2

3-methyl-4-(ethanesulfonamido)phenyl N-methylcarbamate

Ethanesulfonyl chloride (2.2g., 0.0171 mole) was added dropwise to a stirred solution of 3-methyl-4-aminophenyl N-methylcarbamate (3.0g., 0.0166 mole) in 20 ml. of pyridine. The temperature rose to a maximum of 38° C. and then subsided. Stirring was continued at ambient temperature for one hour, and the reaction mixture poured into excess water to give an insoluble precipitate. Recrystallization from ethanol-water gave the product as a beige powder, m.p. 146.5°–48.5° C.

EXAMPLE 3

3-methyl-4-(n-propanesulfonamido)phenyl N-methylcarbamate

According to the general procedure described in Example 1-C, 3-methyl-4-aminophenyl N-methylcarbamate (4.0g., 0.022 mole) was reacted with n-propanesulfonyl chloride (31.5g., 0.022 mole) and triethylamine (2.47g., 0.024 mole) in benzene. The product (4.0g.) showed the characteristic carbonyl absorption at 5.8$\mu$ in the infrared (KBr).

EXAMPLE 4

3-methyl-4-(n-butanesulfonamido)phenyl N-methylcarbamate

Butanesulfonyl chloride (2.6g., 0.017 mole) was added dropwise to a mixture of 3-methyl-4-aminophenyl N-methylcarbamate (3.0g., 0.017 mole), triethylamine (1.85g., 0.018 mole) and benzene (50 ml.). After refluxing for two hours, the reaction mixture was washed in a separatory funnel with water. The organic phase was dried with anhydrous magnesium sulfate and upon removal of the solvent the product was isolated as a dark oil (3.15g.).

EXAMPLE 5

3-methyl-4-(methoxyacetamido)phenyl N-methylcarbamate 3-methyl-4-aminophenyl N-methylcarbamate (3.6g. 0.02 mole) was dissolved in 35 ml. of benzene and 25 ml. of acetonitrile along with triethylamine (2.23g., 0.022 mole). To this stirred solution was added dropwise a solution of methoxyacetyl chloride in benzene. An exotherm to 45° C. was noted as solids began to form. Further heating at reflux for one hour yielded 2.4g. of Et$_3$N.HCl upon filtration. Solvent removal from the filtrate under reduced pressure gave a product which was recrystallized from ethanol-water. The tan solid (2.4g.) melted at 129.5°–132° C. and the infrared spectrum (KBr) displayed the characteristic double carbonyl (5.7 $\mu$ and 5.95 $\mu$).

EXAMPLE 6

3-methyl-4-(ethoxyacetamido)phenyl N-methylcarbamate

According to the procedure of Example 5, 3-methyl-4-aminophenyl N-methylcarbamate was reacted with ethoxyacetyl chloride to yield the desired product m.p. 118°–21° C.

EXAMPLE 7

3-methyl-4-(n-propoxyacetamido)phenyl N-methylcarbamate

According to the procedure of Example 5, 3-methyl-4-aminophenyl N-methylcarbamate was reacted with n-propoxyacetyl chloride to yield a viscous oil as the product.

EXAMPLE 8

3-methyl-4-($\alpha$-phenoxypropionamido)phenyl N-methylcarbamate 3-methyl-4-aminophenyl N-methylcarbamate (1.8g., 0.01 mole), triethylamine (1.31g., 0.013 mole), and a solvent mixture of acetonitrile (20 ml.) and benzene (20 ml.) was stirred while a benzene solution of $\alpha$-phenoxypropionyl chloride was added dropwise. The resulting mixture was refluxed for a short time, cooled, and solvents removed under reduced pressure to yield a tacky residue. This residue was dissolved in a minimum of hot 50% aqueous ethanol. Addition of more water and cooling produced a white precipitate of the desired product (3 grams, m.p. 123°–25° C.).

EXAMPLE 9

3-methyl-4-(trichloroacetamido)phenyl N-methylcarbamate

To a slurry of 3-methyl-4-aminophenyl N-methylcarbamate (1.8g., 0.01 mole), triethylamine (1.11g., 0.011 mole), and 25 ml. of benzene was added trichloroacetyl chloride (2.0g., 0.011 mole) dropwise. After refluxing for one hour, the reaction mixture was poured into water and the resulting solid product was filtered (3.05g., m.p. 185°–87° C.).

EXAMPLE 10

3-methyl-4-(dichloroacetamido)phenyl N-methylcarbamate

A mixture of 3-methyl-4-aminophenyl N-methylcarbamate (1.8 g., 0.01 mole) and dichloroacetic anhydride (2.4g., 0.01 mole) in 25 ml. of benzene was refluxed for about ½ hour. Filtration afforded the product as a white powder (2.35g., m.p. 199°–201° C.).

EXAMPLE 11

3-methyl-4-(3-chloropropionamido)phenyl N-methylcarbamate

According to the general directions described in Example 5, 3-methyl-4-aminophenyl N-methylcarbamate (1.8g., 0.01 mole) was reacted with 3-chloropropionyl chloride (1.52 g., 0.012 mole). The product weighed 2.0g. after recrystallization from ethanol-water and its infrared spectrum showed a double carbonyl absorption at about 5.8 $\mu$ and 6.0 $\mu$.

EXAMPLE 12

3-methyl-4-(trifluoroacetamido)phenyl N-methylcarbamate

The above-named product was obtained by reaction of 3-methyl-4-aminophenyl N-methylcarbamate (1.8g., 0.01 mole) with trifluoroacetic anhydride (2.3g., 0.011 mole) in acetonitrile. The product weighed 2.6g. (m.p. 162°–65° C.).

EXAMPLE 13

3-methyl-4-(chloroacetamido)phenyl N-methylcarbamate

The title product was prepared by reacting 3-methyl-4-aminophenyl N-methylcarbamate (2.5g., 0.0138 mole) with chloroacetic anhydride (2.85g., 0.0166 mole) in benzene giving 3.1g. of white solid (m.p. 169.5°–170.5° C.).

EXAMPLE 14

3-methyl-4-(p-toluenesulfonamido)phenyl N-methylcarbamate p-Toluenesulfonyl chloride (2.1g., 0.011 mole) was added portionwise to a solution of 3-methyl-4-aminophenyl N-methylcarbamate (1.8g., 0.01 mole) in pyridine (15 ml.). An exotherm to about 45° C. resulted and warming was continued at 48° C. for a short time. An excess of water was added and upon stirring and cooling, the product crystallized. The filtered product (3.1g.) was recrystallized from ethanol/water to give material with m.p. 181°–83.5° C.

EXAMPLE 15

3-methyl-4-(methylthioacetamido)phenyl N-methylcarbamate 3-methyl-4-(chloroacetamido)phenyl N-methylcarbamate (3.0g., 0.0117 mole, product of Example 13) was added to a solution of sodium methylmercaptide, prepared by bubbling methylmercaptan into an equivalent of methanolic sodium methoxide solution.

The mixture was stirred overnight and then brought to reflux for one hour. The reaction mixture was stripped of solvent and the residue partitioned between diethylether and water. The ether layer after being washed with water twice was dried with MgSo$_4$, and the product (1.2g.) was isolated as a dark oil. The infrared spectrum of the oil was consistent with its proposed structure.

EXAMPLE 16

3-methyl-4-(chlorodifluoroacetamido)phenyl N-methylcarbamate

According to general procedures outlined above, 3-methyl-4-aminophenyl N-methylcarbamate (2.3g., 0.0128 mole) was reacted with chlorodifluoroacetyl chloride (2.1g., 0.014 mole) in the presence of triethylamine (1.4g., 0.014 mole) and benzene. The product was a light tan solid (1.6g., m.p. 156°–58.5° C.).

EXAMPLE 17

3-methyl-4-(chloromethanesulfonamido)phenyl N-methylcarbamate

According to the procedure of Example 2, 3-methyl-4-aminophenyl N-methylcarbamate (1.8g., 0.01 mole) was reacted with chloromethanesulfonyl chloride (1.63g., 0.011 mole). The product, recrystallized from ethanol/water, was an orange-red solid (m.p. 136.5°–38.5° C.).

EXAMPLE 18

3-methyl-4-(α-chloropropionamido)phenyl N-methylcarbamate

Utilizing benzene and chloroform as the solvent and triethylamine as the acid acceptor, 3-methyl-4-aminophenyl N-methylcarbamate (2.5g., 0.0139 mole) was reacted with α-chloropropionyl chloride (1.79g., 0.0141 mole) to yield the desired product as a white powder (3.6g.). Recrystallization from ethanol/water to give material with m.p. 167°–70° C.

EXAMPLE 19

3-methyl-4-(2-furoylamido)phenyl N-methylcarbamate

Using triethylamine (2 ml.) as the acid acceptor, 3-methyl-4-aminophenyl N-methylcarbamate (2.5g., 0.0139 mole) was reacted with 2-furoyl chloride (1.84g., 0.0141 mole) to give a product which upon recrystallization from ethanol/water weighed 2.8g. (m.p. 177°–78.5° C.).

EXAMPLE 20

3-methyl-4-(carbethoxyamino)phenyl N-methylcarbamate

The reaction of 3-methyl-4-aminophenyl N-methylcarbamate (3.6g., 0.02 mole) with ethyl chloroformate (2.28g., 0.021 mole) and triethylamine (2.23g., 0.022 mole) yielded a beige solid (3.6g., m.p. 153°–55° C. from ethanol/water).

EXAMPLE 21

3-methyl-4-(carbo-n-propoxyamino)phenyl N-methylcarbamate

The reaction of 3-methyl-4-aminophenyl N-methylcarbamate (3.6g., 0.02 mole) with n-propyl chloroformate (2.57g., 0.021 mole) and triethylamine (2.23g., 0.022 mole) gave the desired product (m.p. 126°–27.5° C. from ethanol/water).

EXAMPLE 22

3,5-Dimethyl-4-(ethanesulfonamido)phenyl N-methylcarbamate 3,5-Dimethyl-4-aminophenyl N-methylcarbamate (1.0g., 0.0052 mole), prepared according to the general directions of A. T. Shulgin, U.S. Pat. No. 3,084,098 was dissolved in 5 ml. of pyridine. To this solution was added ethanesulfonyl chloride (0.68g., and 0.0053 mole) and after being stirred for about 20 minutes the reaction solution was warmed briefly at 42° C. Quenching the reaction solution in excess water yielded brown solids which upon being recrystallized from ethanol/water melted at 171°–73° C. (0.85g.).

EXAMPLE 23

3,5-Dimethyl-4-(n-propanesulfonamido)phenyl N-methylcarbamate

Following the procedure of Example 22, 3,5-dimethyl-4-aminophenyl N-methylcarbamate (0.8g., 0.004 mole) was reacted with n-propanesulfonyl chloride (0.60g., 0.0042 mole) in pyridine. The product (0.8g.) melted at 173°–76° C.

EXAMPLE 24

3,5-Dimethyl-4-(methanesulfonamido)phenyl N-methylcarbamate 3,5-Dimethyl-4-methanesulfonamidophenyl (0.4g., 0.0018 mole) in 20 ml. of acetonitrile was reacted with methyl isocyanate (0.114 g., 0.002 mole) at about 45° C. for two hours. A drop of dibutyltindiacetate was used as a catalyst in this reaction. The waxy residue obtained by removal of solvent from the reaction mixture was recrystallized from ethanol/water to give the product as a tan solid (m.p. 178°–85° C.).

EXAMPLE 25

3,5-Dimethyl-4-(methoxyacetamido)phenyl N-methylcarbamate 3,5-Dimethyl-4-methoxyacetamidophenol (0.8g., 0.0038 mole, m.p. 169°–73° C., prepared by reaction of methoxyacetyl chloride with 3,5-dimethyl-4-aminophenol) was reacted with methyl isocyanate (0.245g., 0.004 mole) in benzeneacetonitrile using a few drops of triethylamine as a catalyst. After stirring the initially clear reaction solution for about two days, the precipitated product was filtered (0.6g., m.p. 179.5°–82° C.).

EXAMPLE 26

3,5-Dimethyl-4-(ethoxyacetamido)phenyl N-methylcarbamate 3,5-Dimethyl-4-ethoxyacetamidophenol (1.1g., 0.0049 mole, m.p. 157°–59° C., prepared by reaction of ethoxyacetyl chloride with 3,5-dimethyl-4-aminophenol) was reacted with methyl isocyanate (0.3g., 0.0053 mole) using benzeneacetonitrile as solvent and triethylamine as a catalyst. The reaction mixture was stirred at ambient temperature for 3½ hours, followed by warming at about 45° C. for 2 hours. Solvents were removed under reduced pressure, and the residual solid recrystallized from diethylether and benzene (m.p. 112.5°–115° C.).

EXAMPLE 27

3,5-Dimethyl-4-(chlorodifluoroacetamido)phenyl N-methylcarbamate

According to the general procedure of Example 25 using diethylether as solvent, 3,5-dimethyl-4-chlorodifluoro acetamidophenol (0.7g., 0.0028 mole) was reacted with methyl isocyanate (0.18g., 0.0031 mole) to give the desired product (m.p. 163°–65° C.).

EXAMPLE 28

2,5-Dimethyl-4-(methoxyacetamido)phenyl N-methylcarbamate 2,5-Dimethyl-4-methoxyacetamido)phenol (1.75g., 0.0084 moles, m.p. 139°–41.5° C. prepared by reaction of methoxyacetyl chloride with 2,5-dimethyl-4-aminophenol) was reacted with methyl isocyanate (0.57g., 0.01 mole) as in Example 25. The product was a tan solid (1.8., m.p. 168°–70° C. from ethanol/water).

EXAMPLE 29

2,5-Dimethyl-4-(chlorodifluoroacetamido)phenyl N-methylcarbamate

As in prior examples, 2,5-dimethyl-4-dimethyl-4-chlorodifluoroacetamidophenol was reacted with methyl isocyanate to give the desired product (m.p. 187°–88° C.).

Utilizing the synthetic methods as just described in the previous examples, the following carbamates were also prepared:

EXAMPLE 30

2,5-Dimethyl-4-(ethanesulfonamido)phenyl N-methylcarbamate (m.p. 133°–35° C.).

EXAMPLE 31

2,5-Dimethyl-4-(n-propanesulfonamido)phenyl N-methylcarbamate (m.p. 147.5°–50.5° C.).

EXAMPLE 32

3,5-Dimethyl-4-(trichloroacetamido)phenyl N-methylcarbamate (m.p. 223°–5° C.).

EXAMPLE 33

3,5-Dimethyl-4-(chloromethanesulfonamido)phenyl N-methylcarbamate (m.p. 164°–7° C.).

EXAMPLE 34

3,5-Dimethyl-4-(n-butanesulfonamido)phenyl N-methylcarbamate (m.p. 143°–45.5° C.).

EXAMPLE 35

3-Methyl-4-(cyclopropanecarboxamido)phenyl N-methylcarbamate (m.p. 174°–7° C.).

The compounds of this invention have been found to exhibit considerable biological activity. They are especially potent pesticides when used to control or combat important agricultural pests. These compounds can be used in various ways to achieve biological action. They can be applied per se, as solids or in vaporized form, but are preferably applied as the toxic components in pesticidal compositions of the compound and a carrier. The compositions can be applied as dusts, as liquid sprays, or as gas-propelled sprays and can contain, in addition to a carrier, additives such as emulsifying agents, wetting agents, binding agents, gases compressed to the liquid state, odorants, stabilizers and the like. A wide variety of liquid and solid carriers can be used in the pesticidal compositions. Non-limiting examples of liquid carriers include water; organic solvents such as alcohols, ketones, amides, and esters; mineral oils such as kerosene, light oils, and medium oils; and vegetable oils such as cottonseed oil. Non-limiting examples of solid carriers include talc, bentonite, diatomaceous earth, pyrophyllite, fullers earth, gypsum, flours derived from cotton seeds and nut shells, and various natural and synthetic clays having a pH not exceeding about 9.5.

The amount of the compounds of this invention utilized in pesticidal compositions will vary rather widely. It depends to some extent upon the type of composition in which the material is being used, the nature of the condition to be controlled, and the method of application (i.e., spraying, dusting, etc.). In the ultimate pesticidal composition, as applied in the field, pesticide concentrations as low as 0.0001 weight percent of the total composition can be used. In general, compositions, as applied, containing about 0.05 weight percent pesticide in either liquid or solid carrier give excellent results. In some cases, however, stronger dosages up to about 10 weight percent may be required.

In practice, pesticidal compositions are usually prepared in the form of concentrates, which are diluted in the field to the concentration desired for application. For example, the concentrate can be a wettable powder containing large amounts of the compound of this invention, a carrier (e.g. attapulgite or other clay), and wetting and dispersing agents. Such powders can be diluted prior to application, by dispersing it in water to obtain a sprayable suspension containing the concentration of pesticide desired for application. Other concentrates can be solutions that can be later diluted, e.g. with kerosene. Thus, it is within the contemplation of this invention to provide pesticidal compositions containing up to about 80 percent, by weight of the composition, of a pesticidal compound of this invention. Accordingly, depending upon whether it is ready for application or it is in concentrated form, the contemplated pesticidal compositions contain between about 0.0001 percent and about 80 percent, by weight of the compositions, of a pesticidal compound of this invention and a carrier, liquid or solid, as defined hereinbefore.

INSECTICIDE TEST METHODS

Bait Test [Housefly (adult)]

Method of Treatment

One milliliter of an aqueous solution or suspension of the candidate compound is pipetted into a 9 cm. petri dish containing filter paper and 0.1 gm. granular sugar. Ten adults are admitted and the dish is closed.

Method of Recording Results

Knockdown is recorded after 60 minutes and mortality after 24–75 hours. Compounds which produce 90% mortality are reevaluated at lower concentrations and in secondary tests. Mode of action may be by stomach poison, contact or vapor.

| Systemic Test-Root Uptake (Water Solution) | |
|---|---|
| Primary Screen | Secondary Screen |
| Mexican Bean Beetle (Larva) | Southern Armyworm (Larva) |

Method of Treatment

Young lima bean seedlings growing in sand-soil or other suitable medium are removed and the roots thoroughly washed. The seedlings are placed immediately in a water solution containing a 50 ppm concentration of the test material. One to three days later the seedlings are infested with 5–10 individuals by careful transfer with a camel's hair brush. Each treatment is replicated two times.

Method of Recording Results

Mortality is recorded 72 hours after the seedlings are infested. Compounds active at 50 ppm are retested at lower concentrations of 10 and 1 ppm.

Larvicide/Growth Regulant Test (Yellow Fever Mosquito larvae)

Method of Treatment

The rearing medium is treated prior to infestation. For mosquito larvae this consists of 10 ml. of water containing 10 ppm. of the candidate compound in a plastic cup. Food is added after infesting with 5 last-instar larvae. The cup is than capped. Variants employ dry meal as treated food for flour beetles and semi-synthetic diets for lepidopterous larvae.

Method of Recording Results

Mortality (larvicide) is recorded after 24 hours and survivors are observed through pupal and adult molts for abnormalities (growth regulant).

Ovicide/Larvicide Test (Boll Weevil egg)

Method of Treatment

Boll Weevil eggs are received from the USDA deposited on the surface of larval diet in 9 cm. petri dishes. A segment of this egg-bearing medium, transferred to a filter paper in a clean petri dish, is treated with 2 ml. of an aqueous solution or suspension of the candidate compound, and the dish is closed.

Method of Recording Results

Observations are made periodically for ovicidal, larvicidal and growth regulant activity through adult emergence.

Stomach Poison - Foliar Dip Test

Primary Screen
Southern Armyworm (Larva)
Mexical Bean Beetle (Larva)

Method of Treatment

Lima bean leaves of a uniform size are momentarily dipped in a 500 ppm. water-acetone of the test material. Treated leaves are placed on moistened filter paper in 9 cm. petri dishes and allowed to air dry before being infested. The dishses are then closed.

Method of Recording Results

Mortality and retarded feeding is recorded 72 hours after infestation. Compounds active at 500 ppm. are retested at 100 and 10 ppm.

PERCENT CONTROL CLASSIFICATION KEY

The following percent control classification key is utilized in all insect and mite screening tests:

| Index No. | % Control |
|---|---|
| 1 | 0 |
| 2 | 10 - 20 |
| 3 | 30 |
| 4 | 40 |
| 5 | 50 |
| 6 | 60 |
| 7 | 70 |
| 8 | 80 |
| 9 | 90 |
| 10 | 100 |

The compounds of Examples 1 through 35 were subjected to the aforedescribed insecticide tests. Test concentrations and results are set forth in Tables II and IIa.

TABLE II

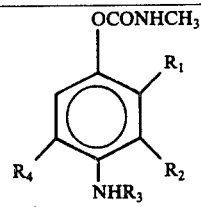

| Ex. No. | $R_1$ | $R_2$ | $R_3$ | $R_4$ | Housefly-Bait. 500 | 100 | 1 | Mexican Bean Beetle-Systemic 50 | 10 | 1 | Southern Armyworm-Systemic 50 | 10 | 1 |
|---|---|---|---|---|---|---|---|---|---|---|---|---|---|
| 1 | H | $CH_3$ | $SO_2CH_3$ | H | | | | 10 | 5 | 2 | 10 | 3 | 1 |
| 2 | H | $CH_3$ | $SO_2C_2H_5$ | H | 1 | | | 10 | 2 | 1 | 1 | | |
| 3 | H | $CH_3$ | $SO_2$n-$C_3H_7$ | H | 6 | | | 10 | | | 1 | | |
| 4 | H | $CH_3$ | $SO_2$n-$C_4H_9$ | H | 10 | 1 | 1 | 5 | | | 1 | | |
| 5 | H | $CH_3$ | $COCH_2OCH_3$ | H | 10 | | 6 | 1 | 10 | 2 | 1 | | |
| 6 | H | $CH_3$ | $COCH_2OC_2H_5$ | H | 10 | | | 10 | 2 | 1 | 6 | 1 | 1 |
| 7 | H | $CH_3$ | $COCH_2$On-$C_3H_7$ | H | 1 | | | 10 | 9 | 1 | 10 | 4 | 1 |
| 8 | H | $CH_3$ | $COCH(CH_3)$—O—$C_6H_5$ | H | 1 | | | 10 | 10 | 1 | 10 | 1 | 1 |
| 9 | H | $CH_3$ | $COCCl_3$ | H | 1 | | | 10 | 3 | 1 | 4 | 1 | 1 |
| 10 | H | $CH_3$ | $COCHCl_2$ | H | 1 | | | 10 | 10 | 1 | 10 | 1 | 1 |
| 11 | H | $CH_3$ | $COCH_2CH_2Cl$ | H | 10 | | | 10 | 1 | 1 | 10 | 10 | 5 |
| 12 | H | $CH_3$ | $COCF_3$ | H | 10 | | | 10 | 10 | 1 | 10 | 3 | 1 |
| 13 | H | $CH_3$ | $COCH_2Cl$ | H | 1 | | | 10 | 2 | 1 | 1 | | |
| 14 | H | $CH_3$ | $SO_2$—$C_6H_4$—$CH_3$ | H | 1 | | | 1 | | | 1 | | |
| 15 | H | $CH_3$ | $COCH_2SCH_3$ | H | 1 | | | 1 | | | | | |
| 16 | H | $CH_3$ | $COCF_2Cl$ | H | 4 | | | 10 | 10 | 2 | 10 | 10 | 1 |
| 17 | H | $CH_3$ | $SO_2CH_2Cl$ | H | | | | 10 | 1 | 1 | 10 | 1 | 1 |
| 18 | H | $CH_3$ | $COCH(Cl)CH_3$ | H | 1 | | | 10 | | | 10 | 7 | 1 |
| 19 | H | $CH_3$ | CO-furyl | H | 10 | | | 10 | 10 | 1 | 10 | | |
| 20 | H | $CH_3$ | $CO_2C_2H_5$ | H | 10 | 9 | 1 | 10 | 9 | 1 | 10 | 9 | 1 |
| 21 | H | $CH_3$ | $CO_2$n-$C_3H_7$ | H | 10 | 10 | 1 | 10 | 1 | 10 | 6 | 1 | |
| 22 | H | $CH_3$ | $SO_2C_2H_5$ | $CH_3$ | 5 | | | 3 | | | | | |
| 23 | H | $CH_3$ | $SO_2$n-$C_3H_7$ | $CH_3$ | 4 | | | 10 | 1 | 1 | | | |
| 24 | H | $CH_3$ | $SO_2CH_3$ | $CH_3$ | 10 | | | 8 | | | | | |
| 25 | H | $CH_3$ | $COCH_2OCH_3$ | $CH_3$ | 10 | | | 10 | | | 6 | | |
| 26 | H | $CH_3$ | $COCH_2OC_2H_5$ | $CH_3$ | 4 | 1 | 1 | 10 | | | | | |
| 27 | H | $CH_3$ | $COCF_2Cl$ | $CH_3$ | 9 | 9 | 1 | 10 | 1 | 1 | | | |
| 28 | $CH_3$ | H | $COCH_2OCH_3$ | $CH_3$ | 10 | 2 | 1 | 3 | | | | | |
| 29 | $CH_3$ | H | $COCF_2Cl$ | $CH_3$ | 1 | | | 10 | 8 | 1 | | | |
| 30 | $CH_3$ | H | $SO_2C_2H_5$ | $CH_3$ | 1 | | | 1 | | | | | |
| 31 | $CH_3$ | H | $SO_2$-n-$C_3H_7$ | $CH_3$ | 1 | | | 8 | 1 | | | | |
| 32 | H | $CH_3$ | $COCl_3$ | $CH_3$ | 3 | | | 10 | 1 | | | | |
| 33 | H | $CH_3$ | $SO_2CH_2Cl$ | $CH_3$ | 10 | 5 | | 10 | 1 | | | | |
| 34 | H | $CH_3$ | $SO_2$-n-$C_4H_9$ | $CH_3$ | 12 | | | 2 | | | | | |
| 35 | H | $CH_3$ | CO-cyclopropyl | H | 10 | | | 10 | 2 | 1 | | | |

TABLE IIa

| Example No. | Yellow Fever Mosquito-Larvicide/Growth Reg. 10 | 1 | 0.1 | Cotton Boll Weevil-Ovicide/Larvicide 500 | 100 | 10 | Southern Armyworm Stomach Poison 500 | 100 | 10 | Mexican Bean Beetle-Stomach Poison 500 | 100 | 10 |
|---|---|---|---|---|---|---|---|---|---|---|---|---|
| 1 | | | | | | | 1 | | | | | |
| 2 | 1 | | | 9 | | | 10 | 8 | 1 | 10 | 6 | 4 |
| 3 | 1 | | | 10 | | | 10 | 10 | 1 | 10 | 6 | 2 |
| 4 | 8 | 1 | 1 | 9 | | | 10 | 8 | 1 | 10 | 10 | 2 |
| 5 | 4 | 2 | 1 | 10 | 10 | 3 | 10 | 10 | 8 | 10 | 6 | 8 |
| 6 | 6 | | | 10 | | | 10 | 10 | 7 | 10 | 9 | 4 |
| 7 | 10 | | | 10 | | | 10 | 8 | 1 | 10 | 10 | 5 |
| 8 | 1 | | | 4 | | | 10 | 10 | 1 | 10 | 10 | 7 |
| 9 | 1 | | | 10 | | | 10 | 10 | 6 | 10 | 10 | 9 |
| 10 | 10 | | | 1 | | | 10 | 10 | 1 | 10 | 10 | 3 |

TABLE IIa-continued

| Example No. | Yellow Fever Mosquito-Larvicide/Growth Reg. | | | Cotton Boll Weevil-Ovicide/Larvicide | | | Southern Armyworm Stomach Poison | | | Mexican Bean Beetle-Stomach Poison | | |
| --- | --- | --- | --- | --- | --- | --- | --- | --- | --- | --- | --- | --- |
| | 10 | 1 | 0.1 | 500 | 100 | 10 | 500 | 100 | 10 | 500 | 100 | 10 |
| 11 | | | | 9 | | | 10 | 10 | 1 | 10 | 10 | 8 |
| 12 | 10 | | | 10 | | | 10 | 10 | 1 | 10 | 10 | 6 |
| 13 | 1 | | | 8 | | | 10 | 10 | 4 | 10 | 8 | 1 |
| 14 | 4 | | | | | | 1 | | | 1 | | |
| 15 | 1 | | | 1 | 4 | | 5 | | | | | |
| 16 | | | | | | | 10 | 10 | 5 | 10 | 10 | 10 |
| 17 | | | | | | | 10 | 10 | 1 | 10 | 10 | 4 |
| 18 | 1 | | | 10 | | | 10 | 10 | 1 | 10 | 10 | 1 |
| 19 | 1 | | | 10 | | | 10 | 10 | 1 | 10 | 10 | 1 |
| 20 | 8 | 4 | 1 | 10 | 10 | | 9 | 7 | 1 | 10 | 9 | 3 |
| 21 | 8 | 4 | 1 | 5 | | | 9 | 1 | 1 | 10 | 10 | 5 |
| 22 | 6 | | | 4 | | | 10 | 10 | 8 | 9 | 8 | 2 |
| 23 | 4 | | | 9 | | | 10 | 5 | 2 | 10 | 9 | 2 |
| 24 | 2 | | | 1 | | | 10 | | | 2 | | |
| 25 | 1 | | | | | | 10 | 1 | 1 | 10 | 10 | 1 |
| 26 | 6 | 2 | 2 | 4 | 1 | 1 | 10 | 8 | 1 | 10 | 10 | 10 |
| 27 | 6 | | | 7 | | | 10 | 10 | 1 | 10 | 10 | 4 |
| 28 | 6 | | | 10 | 7 | 1 | 10 | 1 | 1 | 10 | 10 | 8 |
| 29 | 4 | | | 9 | 9 | | 10 | 1 | 1 | 10 | 10 | 3 |
| 30 | | | | 1 | | | 10 | 1 | | 1 | | |
| 31 | | | | 1 | | | 2 | | | 8 | 3 | |
| 32 | | | | 8 | | | 10 | 1 | | 10 | 7 | 1 |
| 33 | | | | 10 | | 10 | 8 | | 10 | 8 | 7 | |
| 34 | | | | | | | 5 | 1 | | 10 | 4 | |
| 35 | 1 | | | 10 | | | 1 | | | 10 | 7 | 3 |

Although the present invention has been described with preferred embodiments, it is to be understood that modifications and variations may be resorted to, without departing from the spirit and scope of this invention, as those skilled in the art will readily understand. Such modifications and variations are considered to be within the purview and scope of the appended claims.

What is claimed is:

1. A compound having the structure:

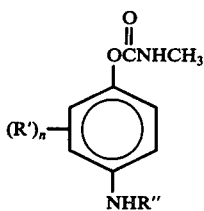

wherein R' is ($C_1$-$C_5$) alkyl, Cl, or ($C_1$-$C_4$) alkoxy; n is 1 to 3; R" is -$SO_2$R''' wherein R''' is ($C_1$-$C_4$) alkyl, ($C_3$-$C_6$) cycloalkyl, ($C_1$-$C_4$) monohaloalkyl, phenyl, or tolyl or R" is

wherein R'''' is ($C_1$-$C_4$) alkoxy ($C_1$-$C_4$) alkyl, ($C_1$-$C_4$) haloalkyl, phenoxy ($C_1$-$C_4$) alkyl, ($C_1$-$C_4$) alkylthio ($C_1$-$C_4$) alkyl, and furyl.

2. A compound of claim 1, wherein said compound is 3-methyl-4-(methoxyacetamido)phenyl N-methylcarbamate.

3. A compound of claim 1, wherein said compound is 3-methyl-4-(trichloroacetamido)phenyl N-methylcarbamate.

4. A compound of claim 1, wherein said compound is 3-methyl-4-(3-chloropropionamido)phenyl N-methylcarbamate.

5. A compound of claim 1, wherein said compounds is 3-methyl-4-(chlorodifluoroacetamido)phenyl N-methylcarbamate.

6. A compound of claim 1, wherein said compounds is 3,5-dimethyl-4-(ethanesulfonamido)phenyl N-methylcarbamate.

7. A compound of claim 1, wherein said compound is 3-methyl-4-(propoxyacetamido)phenyl N-methylcarbamate.

8. A compound of claim 1, wherein said compound is 3-methyl-4-(α-phenoxypropionamido)phenyl N-methylcarbamate.

9. A compound of claim 1, wherein said compound is 3-methyl-4-(dichloroacetamido)phenyl N-methylcarbamate.

10. A compound of claim 1, wherein said compound is 3-methyl-4-(trifluoroacetamido)phenyl N-methylcarbamate.

11. A compound of claim 1, wherein said compound is 3-methyl-4-(2-furoylamido)phenyl N-methylcarbamate.

12. A compound of claim 1, wherein said compound is 3,5-dimethyl-4-(ethoxyacetamido)phenyl N-methylcarbamate.

13. A compound of claim 1, wherein said compound is 3,5-dimethyl-4-(chloromethanesulfonamido)phenyl N-methylcarbamate.

14. An insecticidal composition comprising a carrier and between about 0.0001 percent and about 80 percent, by weight of said composition of a compound having the structure:

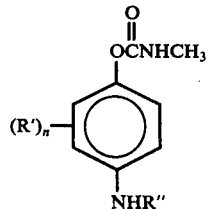

wherein R' is ($C_1$-$C_5$) alkyl, Cl, or ($C_1$-$C_4$) alkoxy; n is 1 to 3; R" is —$SO_2$ R''', wherein R'''is ($C_1$-$C_4$) alkyl, ($C_3$-$C_6$) cycloalkyl, ($C_1$-$C_4$) monohaloalkyl, phenyl, or tolyl or R" is

wherein R'''' is (C$_1$-C$_4$) alkoxy (C$_1$-C$_4$) alkyl, (C$_1$-C$_4$) haloalkyl, phenoxy (C$_1$-C$_4$) alkyl, (C$_1$-C$_4$) alkylthio (C$_1$-C$_4$) alkyl, and furyl.

15. A composition of claim 14, wherein said compound is 3-methyl-4-(methoxyacetamido)phenyl N-methylcarbamate.

16. A composition of claim 14, wherein said compound is 3-methyl-4-(trichloroacetamido)phenyl N-methylcarbamate.

17. A composition of claim 14, wherein said compound is 3-methyl-4-(3-chloropropionamido)phenyl N-methylcarbamate.

18. A composition of claim 14, wherein said compound is 3-methyl-4-(chlorofluoroacetamido)phenyl N-methylcarbamate.

19. A composition of claim 14, wherein said compound is 3,5-dimethyl-4-(ethanesulfonamido)phenyl N-methylcabamate.

20. A composition of claim 14, wherein said compound is 3-methyl-4-(propoxyacetamido)phenyl N-methylcarbamate.

21. A composition of claim 14, wherein said compound is 3-methyl-4-(α-phenoxypropionamido)phenyl N-methylcarbamate.

22. A composition of claim 14, wherein said compound is 3-methyl-4-(dichloroacetamido)phenyl N-methylcarbamate.

23. A composition of claim 14, wherein said compound is 3-methyl-4-(trifluoroacetamido)phenyl N-methylcarbamate.

24. A composition of claim 14, wherein said compound is 3-methyl-4-(2-furoylamido)phenyl N-methylcarbamate.

25. A composition of claim 14, wherein said compound is 3,5-dimethyl-4-(ethoxyacetamido)phenyl N-methylcarbamate.

26. A composition of claim 14, wherein said compound is 3,5-dimethyl-4-(chloromethanesulfonamido)phenyl N-methylcarbamate.

27. The method for combatting insects which comprises contacting them, their larvae, or their ova with an insecticidally effective amount of a compound having the structure:

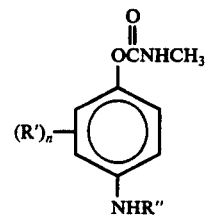

wherein R' is (C$_1$-C$_5$) alkyl, Cl, or (C$_1$-C$_4$) alkoxy; $n$ is 1 to 3; R'' is -SO$_2$R''', wherein R''' is (C$_1$-C$_4$) alkyl, (C$_3$-C$_6$) cycloalkyl, (C$_1$-C$_4$) monohaloalkyl, phenyl, or tolyl or R'' is

wherein R'''' is (C$_1$-C$_4$) alkoxy (C$_1$-C$_4$) alkyl, (C$_1$-C$_4$) haloalkyl, phenoxy (C$_1$-C$_4$) alkyl, (C$_1$-C$_4$) alkylthio (C$_1$-C$_4$) alkyl, and furyl.

28. The method of claim 27, wherein said compound is 3-methyl-4-(methoxyacetamido)phenyl N-methylcarbamate.

29. The method of claim 27, wherein said compound is 3-methyl-4-(trichloroacetamido)phenyl N-methylcarbamate.

30. The method of claim 27, wherein said compound is 3-methyl-4-(3-chloropropionamido)phenyl N-methylcarbamate.

31. The method of claim 27, wherein said compound is 3-methyl-4-(chlorodifluoroacetamido)phenyl N-methylcarbamate.

32. The method of claim 27, wherein said compound is 3,5-dimethyl-4-(ethanesulfonamido)phenyl N-methylcarbamate.

33. The method of claim 27, wherein said compound is 3-methyl-4-(propoxyacetamido)phenyl N-methylcarbamate.

34. The method of claim 27, wherein said compound is 3-methyl-4-(α-phenoxypropionamido)phenyl N-methylcarbamate.

35. The method of claim 27, wherein said compound is 3-methyl-4-(dichloroacetamido)phenyl N-methylcarbamate.

36. The method of claim 27, wherein said compound is 3-methyl-4-(trifluoroacetamido)phenyl N-methylcarbamate.

37. The method of claim 27, wherein said compound is 3-methyl-4-(2-furoylamido)phenyl N-methylcarbamate.

38. The method of claim 27, wherein said compound is 3,5-dimethyl-4-(ethoxyacetamido)phenyl N-methylcarbamate.

39. The method of claim 27, wherein said compound is 3,5-dimethyl-4-(chloromethanesulfonamido)phenyl N-methylcarbamate.

* * * * *

UNITED STATES PATENT AND TRADEMARK OFFICE
CERTIFICATE OF CORRECTION

PATENT NO. : 4,051,254  
DATED : September 27, 1977  
INVENTOR(S) : L.L. MARAVETZ Page 1 of 3

It is certified that error appears in the above-identified patent and that said Letters Patent are hereby corrected as shown below:

| | |
|---|---|
| Col. 1, line 68 | "includes" should be --include-- |
| Col. 5, line 14 | "yieldig" should be --yielded-- |
| Col. 5, line 65 | "(31.5g.," should be --(3.15g.,-- |
| Col. 10, line 32 Example 29 | "2,5-dimethyl-4-dimethyl-4-" should be --2,5-dimethyl-4-chlorodifluoro-- |
| Col. 13, Table II, Example 4, Under column $R_3$ | "$SO_2n-C_49$" should be --$SO_2n-C_4H_9$-- |
| Col. 14, Table II, Example 5, Under col. Housefly-Bait "100" | Under the column 100 should show the number --6--; under the column 1, "6" should be --1-- |
| Col. 14, Table II, Example 5, Under col. Mexican Bean Beetle "50" | Under the column 50, "1" should be --10-- |
| Column 14, Table II, Example 5, Under col. Mexican Bean Beetle "10" | Under the column 10, "10" should be --2-- |
| Column 14, Table II, Example 5, Under col. Mexican Bean Beetle "1" | Under the column 1, "2" should be --1-- |

UNITED STATES PATENT AND TRADEMARK OFFICE
CERTIFICATE OF CORRECTION

PATENT NO. : 4,051,254

DATED : September 27, 1977

INVENTOR(S) : L.L. MARAVETZ

Page 2 of 3

It is certified that error appears in the above-identified patent and that said Letters Patent are hereby corrected as shown below:

| | |
|---|---|
| Col. 14, Table II, Example 5, Under Column - Southern Armyworm Systemic "50" | Under Column 50 omit "1" |
| Col. 14, Table II, Example 20, Under Column - Southern Armyworm Systemic "50" | Under Column 50 omit "10" |
| Col. 14, Table II, Example 20, Under Column - Southern Armyworm Systemic "10" | Under Column 10 omit "9" |
| Col. 14, Table II, Example 20, Under Column - Southern Armyworm Systemic "1" | Under Column 1 omit "1" |
| Col. 14, Table II, Example 21, Under Column - Mexican Bean Beetle "10" | Under Column 10, "1" should be --6-- |
| Col. 14, Table II, Example 21, Under Column - Mexican Bean Beetle "1" | Under Column 1, "10" should be --1-- |
| Col. 14, Table II, Example 20, Under Column - Southern Armyworm Systemic "50" | Under Column 50 omit "10" |
| Col. 14, Table II, Example 21, Under Column - Southern Armyworm Systemic "50" | Under Column 50 omit "6" |

UNITED STATES PATENT AND TRADEMARK OFFICE
CERTIFICATE OF CORRECTION

PATENT NO. : 4,051,254

DATED : September 27, 1977

Page 3 of 3

INVENTOR(S) : L.L. MARAVETZ

It is certified that error appears in the above—identified patent and that said Letters Patent are hereby corrected as shown below:

Col. 14, Table II, Example 20, Under Column - Southern Armyworm Systemic "10"   Under Column 10 omit "9"

Col. 14, Table II, Example 21, Under Column - Southern Armyworm Systemic "10"   Under Column 10 omit "1"

Col. 14, Table II, Example 20, Under Column - Southern Armyworm Systemic "1"    Under Column 1 omit "1"

Col. 14, Table II, Example 34, Under Column - Housefly Bait "500"   Under Column 500, "12" should be --2--

Col. 15, Table IIa, Example 19, Under Column - Mexican Bean Beetle Stomach Poison "10"   Under Column 10, "1" should be --9--

Signed and Sealed this

Sixteenth Day of May 1978

[SEAL]

Attest:

RUTH C. MASON
Attesting Officer

LUTRELLE F. PARKER
Acting Commissioner of Patents and Trademarks